United States Patent [19]

Drabek et al.

[11] 4,305,957
[45] Dec. 15, 1981

[54] N-(2-ISOBUTYRONITRILESULFENYL)-N-METHYL CARBAMATES AND THEIR USE IN COMBATING INSECT PESTS

[75] Inventors: Jozef Drabek, Oberwil, Switzerland; Manfred Böger, Weil am Rhein, Fed. Rep. of Germany

[73] Assignee: Ciba-Geigy Corporation, Ardsley, N.Y.

[21] Appl. No.: 172,907

[22] Filed: Jul. 28, 1980

[30] Foreign Application Priority Data

Aug. 10, 1979 [CH] Switzerland .......................... 7372/79
Jun. 27, 1980 [CH] Switzerland .......................... 4962/80

[51] Int. Cl.³ .................... A01N 47/18; C07D 307/86; A01N 47/22; C07C 125/067
[52] U.S. Cl. .................................... 424/285; 424/278; 424/282; 424/300; 260/340.5 R; 260/340.9 R; 260/346.73; 260/465 D
[58] Field of Search ....... 260/346.73, 465 D, 340.5 R, 260/340.9 R; 424/278, 282, 285, 300

[56] References Cited

U.S. PATENT DOCUMENTS 3,847,951 11/1974 Kohn et al. .................... 260/346.73
4,179,514 12/1979 D'Silva .............................. 424/277

OTHER PUBLICATIONS

Hackh's Chemical Dictionary–McGraw Hill, N.Y. City, (1969) p. 665.

Primary Examiner—Henry R. Jiles
Assistant Examiner—Bernard Dentz
Attorney, Agent, or Firm—Frederick H. Rabin

[57] ABSTRACT

N-(2-Isobutyronitrilesulfenyl)-N-methyl carbamates of the formula

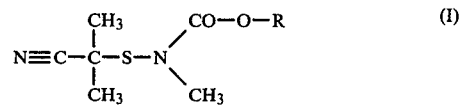

wherein R is 2,2-dimethyl-(2H,3H)-dihydrobenzofuran-7-yl, α-naphthyl,

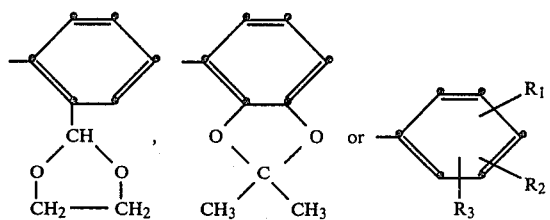

and $R_1$, $R_2$ and $R_3$ are each hydrogen, $C_1$–$C_5$-alkoxy or $C_1$–$C_5$-alkylthio. Processes for producing these compounds and their use for combating pests on animals and on plants are described.

6 Claims, No Drawings

N-(2-ISOBUTYRONITRILESULFENYL)-N-METHYL CARBAMATES AND THEIR USE IN COMBATING INSECT PESTS

The present invention relates to novel N-(2-isobutyronitrilesulfenyl)-N-methyl carbamates which have an action against insect pests, to processes for producing these carbamates, to pesticidal compositions containing them as active ingredients, and to processes for combating insect pests by application of the novel compounds.

The N-(2-isobutyronitrilesulfenyl)-N-methyl carbamates correspond to the formula I

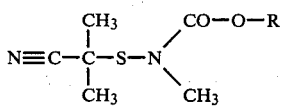

wherein R is 2,2-dimethyl-(2H,3H)-dihydrobenzofuran-7-yl, α-naphthyl,

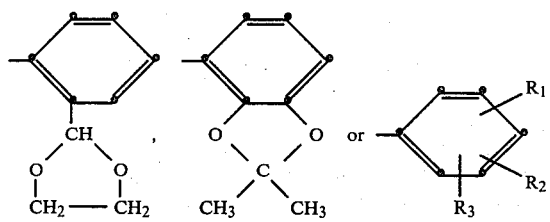

and $R_1$, $R_2$ and $R_3$ are each hydrogen, $C_1$-$C_5$-alkyl, $C_1$-$C_5$-alkoxy or $C_1$-$C_5$-alkylthio.

The alkyl, alkoxy and alkylthio groups for $R_1$, $R_2$ and $R_3$ can be straight-chain or branched-chain. Examples of such groups are, inter alia: methyl, methoxy, methylthio, ethyl, ethoxy, propyl, propoxy, isopropyl, isopropoxy, or n-, i-, sec- or tert-butyl, or n-pentyl and isomers thereof.

Compounds of the formula I which are preferred on account of their activity are those wherein R is 2,2-dimethyl-(2H,3H)-dihydrobenzofuran-7-yl, α-naphthyl,

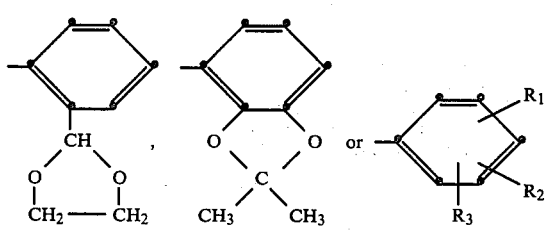

$R_1$ is hydrogen or $C_1$-$C_5$-alkyl, and $R_2$ and $R_3$ are each hydrogen, methyl, isopropoxy or methylthio.

The compounds of the formula I are produced by processes analogous to known processes, for example (a) by reacting a compound of the formula II

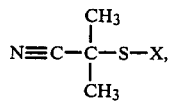

in the presence of a base, with a compound of the formula III

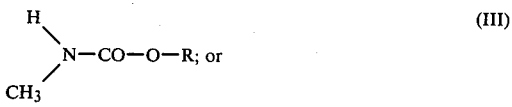

(b) by reacting a compound of the formula IV

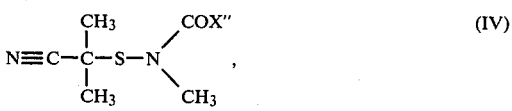

in the presence of a base, with a compound of the formula V

the meaning of R in the formulae II to V being as defined for the formula I, X' being a halogen atom, particularly a chlorine atom, and X" being a halogen atom, especially a fluorine atom.

The processes (a) and (b) are performed at a reaction temperature of between −50° C. and +130° C., preferably between −10° C. and +100° C., under normal or slightly elevated pressure, and in the presence of a solvent or diluent which is inert to the reactants.

Suitable bases for these processes are in particular: tertiary amines, such as trialkylamines, pyridines and dialkylanilines, also hydroxides, oxides, or carbonates and bicarbonates of alkali metals and alkaline-earth metals, as well as alkali metal alcoholates, for example potassium tert-butylate and sodium methylate.

Suitable solvents or diluents are for example: ethers and ethereal compounds, such as diethyl ether, di-isopropyl ether, dioxane or tetrahydrofuran; aliphatic and aromatic hydrocarbons, especially benzene, toluene or xylenes; and ketones, such as acetone, methyl ethyl ketone and cyclohexanone.

The starting materials of the formulae II, III and V used in the processes described in the foregoing are known, or can be produced by methods analogous to known methods.

The starting materials of the formula IV are known and can be readily obtained from known precursors, for example by reacting a compound of the already defined formula II, in the presence of a base, with a compound of the formula VI

wherein X" has the meaning already defined.

The process for producing the starting materials of the formula IV is advantageously performed in the presence of a solvent or diluent inert to the reactants, at a reaction temperature of −50° C. to +130° C., and under normal pressure. Suitable bases and solvents applicable for this process are the substances already mentioned for the processes (a) and (b) described above.

The compounds of the formula I are suitable for combating various pests on animals and plants. These compounds are particularly suitable for combating all development stages of insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera. Furthermore, the compounds of the formula I have a valuable action against nematodes parasitic on plants, and also against Acarina, particularly ectoparasitic Acarina (mites and ticks), for example of the families Ixodidae, Argasidae and Dermanyssidae. Compounds of the formula I are especially suitable for controlling insects that damage plants, in particular insects that damage plants by eating, in crops of ornamental plants and productive plants, particularly in cotton crops (for example against *Spodoptera littoralis* and *Heliothis virescens*), in vegetable crops (for example against *Leptinotarsa decemlineata* and *Myzus persicae*) and in rice crops (for example against rice grasshoppers). Active substances of the formula I also have a very favourable action against flies, such as *Musca domestica*, and against mosquito larvae. The compounds of the formula I are in addition characterised by a broad ovicidal and ovilarvicidal action.

The compounds of the formula I can as a rule be used in a known manner either in an unchanged form or, together with auxiliaries customarily used in formulation practice, in the form of preparations, for example emulsion concentrates, suspension concentrates, directly sprayable solutions or dilutable solutions, diluted emulsions, wettable powders, soluble powders, dusts or granulates, and also superfine encapsulations in polymeric substances and the like. The form of application, such as spraying, atomising, dusting, scattering or pouring, is governed entirely by the purpose of application. It is to be ensured however in this respect that the biological behaviour of the active substance of the formula I is not significantly affected by the method of application, or by the type and amount of auxiliaries used for producing the preparation.

The preparations are produced in a known manner, for example by the intimate mixing and/or grinding of the active substances with extenders, that is, with solvents or solid carriers, and optionally with the use of surfaceactive substances (tensides). The solvents can be: aromatic hydrocarbons, preferably the fractions $C_8$ to $C_{12}$, i.e. xylene mixtures up to substituted naphthalenes, aliphatic hydrocarbons, such as cyclohexane or paraffins, alcohols and glycols, as well as ethers and esters thereof, strongly polar solvents, such as dimethylsulfoxide or dimethylformamide, and also water. The solid carriers used, for example for dusts and dispersible powders, are mostly natural mineral fillers. Suitable chemically are in particular calcite, talcum, kaolinite, montmorillonite and attapulgite. In order to improve the physical properties, it is also possible to use highly dispersed silicic acids or highly dispersed absorbent polymers. Suitable granulated carriers are porous types, for example pumice, broken brick, sepiolite and bentonite; and suitable nonsorbent carriers are materials such as calcite or sand. There can also be used a great number of pregranulated materials of inorganic or organic nature, extending from dolomite to pulverised nutshells or corncobs.

Suitable surface-active substances are, depending on the polarity of the active substance of the formula I to be formulated, nonionic, cation-active and/or anion-active tensides having good emulsifying, dispersing and wetting properties.

Suitable anion-active tensides are for example: quaternary ammonium compounds, such as cetyltrimethylammonium bromide. Suitable anion-active tensides are for example: soaps, salts of aliphatic monoesters of sulfuric acid, such as sodium lauryl sulfate, salts of sulfonated aromatic compounds, for example sodium dodecylbenzenesulfonate, sodium-, calcium- and ammonium-lignin sulfonate, butylnaphthalenesulfonate and a mixture of the sodium salts of diisopropyl- and triisopropylnaphthalenesulfonate. Suitable nonionogenic tensides are for example the condensation products of ethylene oxide with fatty alcohols, for example oleyl alcohol or cetyl alcohol, or with alkylphenols, such as octylphenol, nonylphenol and octylcresol. Other nonionic agents are the partial esters derived from long-chain fatty acids and hexite anhydrides, and the condensation products of these partial esters with ethylene oxide and the lecithins.

The nonionogenic, anion-active and cation-active tensides commonly used in formulation practice are described in, inter alia, the following publications:

"McCutcheon's Detergents and Emulsifiers Annual", MC Publishing Corp. Ringewood, N.J.;

Sisely and Wood, "Encyclopedia of Surface Active Agents", Chemical Publishing Co., N.Y.

The preparations as a rule contain 0.1 to 99%, especially 0.1 to 95%, of active substance of the formula I, and at least 0 to 25% of a tenside, as well as 1 to 99.9% of a solid or liquid additive.

The preparations can also contain agents such as stabilisers, antifoam agents, viscosity regulators, binders, adhesives as well as fertiliser additives, to produce special effects.

The active substances of the formula I can be formulated for example as follows: (values in % by weight)

Formulation examples for liquid active substances of the formula I

| Emulsion concentrates | |
|---|---|
| (a) active substance | 20% |
| calcium dodecylbenzenesulfonate | 5% |
| castor oil-polyglycol ether | |
| (36 mols of ethylene oxide) | 5% |
| xylene mixture | 70%; |
| (b) active substance | 40% |
| calcium dodecylbenzenesulfonate | 8% |
| tributylphenol-polyglycol ether | |
| (30 mols of ethylene oxide) | 12% |
| cyclohexanone | 15% |
| xylene mixture | 25%; |
| (c) active substance | 50% |
| tributylphenol-polyglycol ether | 4.2% |
| calcium dodecylbenzenesulfonate | 5.8% |
| cyclohexanone | 20% |
| xylene mixture | 20%. |

Emulsions of any required concentration can be produced from concentrates of this kind by diluting them with water.

| Solutions | |
|---|---|
| (a) active substance | 80% |
| ethylene glycol monomethyl ether; | 20%; |
| (b) active substance | 10% |
| polyethylene glycol 400 | 70% |
| N-methyl-2-pyrrolidone; | 20%; |
| (c) active substance | 5% |
| epoxidised vegetable oil | 1% |
| ligroin (boiling limits 160–190° C.); | 94%; |

| Solutions | | |
|---|---|---|
| (d) | active substance | 95% |
| | epoxidised vegetable oil. | 5%. |

These solutions are suitable for application in the form of drops as small as possible.

| Granulates | | |
|---|---|---|
| (a) | active substance | 5% |
| | kaolin (0.2–0.8 mm) | 94% |
| | highly dispersed silicic acid | 1%; |
| (b) | active substance | 10% |
| | attaclay (0.3–1 mm) | 90%. |

The active substance is dissolved in methylene chloride, the solution is sprayed onto the carrier, and the solvent is subsequently evaporated off in vacuo.

| Dusts | | |
|---|---|---|
| (a) | active substance | 2% |
| | highly dispersed silicic acid | 1% |
| | talcum | 97%; |
| (b) | active substance | 5% |
| | highly dispersed silicic acid | 5% |
| | kaolin (finely divided) | 90%. |

Dusts which are ready for use are obtained by the intimate mixing of the carriers with the active substance.

Formulation examples for solid active substances of the formula I

| Wettable powders | | |
|---|---|---|
| (a) | active substance | 20% |
| | sodium lignin sulfonate | 5% |
| | sodium lauryl sulfate | 3% |
| | silicic acid | 5% |
| | kaolin | 67%; |
| (b) | active substance | 60% |
| | sodium lignin sulfonate | 5% |
| | sodium diisobutylnaphthalenesulfonate | 6% |
| | octylphenol polyglycol ether (7–8 mols of ethylene oxide) | 2% |
| | highly dispersed silicic acid | 27%. |

The active substance is well mixed with the additives and the mixture is thoroughly ground in a suitable mill. There are obtained wettable powders which can be diluted with water to give suspensions of the concentration desired.

| Emulsion concentrate | |
|---|---|
| active substance | 10% |
| octylphenol polyglycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50%. |

Emulsions of any required concentration can be obtained from this concentrate by dilution with water.

| Dust | | |
|---|---|---|
| (a) | active substance | 5% |
| | talcum | 95%; |
| (b) | active substance | 8% |
| | kaolin (finely divided) | 92%. |

Dusts which are ready for use are obtained by mixing the active substance with the carriers, and grinding the mixture in a suitable mill.

| Extruder granulate | |
|---|---|
| active substance | 10% |
| sodium lignin sulfonate | 2% |
| carboxymethylcellulose | 1% |
| kaolin (finely divided) | 87%. |

The active substance is mixed and ground with the additives, and the mixture is subsequently moistened with water. The mixture is extruded and then dried in a stream of air.

| Coated granulate | |
|---|---|
| active substance | 3% |
| polyethylene glycol 200 | 3% |
| kaolin (0.3–0.8 mm) | 94%. |

The finely ground active substance is uniformly applied, in a mixer, to the kaolin moistened with polyethylene glyol. Non-dusty coated granulates are obtained in this manner.

| Suspension concentrate | |
|---|---|
| active substance | 40% |
| ethylene glycol | 10% |
| nonylphenol polyglycol ether (15 mols of ethylene oxide) | 6% |
| sodium lignin sulfonate | 10% |
| carboxymethylcellulose | 1% |
| formalin (37% formaldehyde solution) | 0.2% |
| silicone oil in the form of a 75% emulsion | 0.8% |
| mains water | 32%. |

The finely ground active substance is intimately mixed with the additives. There is thus obtained a suspension concentrate from which can be produced, by dilution with water, suspensions of any concentration required.

EXAMPLE 1

Production process (a) Production of (2-fluorocarbonyl-4-cyano-4-methyl)-2-aza-3-sulfa-pentane (starting material)

34.8 ml of methylisocyanate were added at −50° C., with stirring, to a solution of 11.7 g of anhydrous hydrofluoric acid in 100 ml of toluene, and stirring was continued for 2 hours. To the resulting solution were added 79.4 g of isobutyronitrile-2-sulfenyl chloride, and there were then added dropwise at −50° C. to −20° C., with stirring, 80.85 ml of triethylamine. The reaction mixture was stirred for 2 hours at −20° C., for 1 hour at room temperature, and for 1 hour at 50° C. The formed triethylamine hydrochloride was filtered off with suction, and the filtrate was concentrated in a rotary evaporator. Distillation of the crude product under high vacuum yields (2-fluorocarbonyl-4-cyano-4-methyl)-2-aza-3-sulfa-pentane of the formula

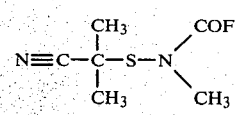

as a yellow liquid (b.p. 78°–80° C./0.25 mbars).

(b) Production of N-(2-isobutyronitrilesulfenyl)-(2,3-dihydro-2,2-dimethyl-7-benzofuranyl)-N-methyl carbamate (final product)

To a solution of 5.5 g of 2,3-dihydro-2,2-dimethyl-7-hydroxybenzofuran in 80 ml of toluene were added, with stirring, 5.95 ml of triethylamine, and there were subsequently added dropwise, at a maximum of 30° C., 5.9 g of (2-fluorocarbonyl-4-cyano-4-methyl)-2-aza-3-sulfa-pentane. The reaction mixture was then stirred for 16 hours at room temperature and for 2½ hours at 40°–50° C., filtered, and concentrated by evaporation. The crude product was taken up in diethyl ether and washed four times with 50 ml of water each time; the organic phase was then dried over $Na_2SO_4$ and finally concentrated by evaporation. By this procedure is obtained N-(2-isobutyronitrilesulfenyl)-(2,3-dihydro-2,2-dimethyl-7-benzofuranyl)-N-methyl carbamate of the formula

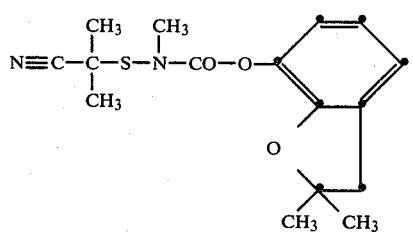

in the form of a yellow oil having a refractive index of $n_D^{21°}$: 1.5293.

The following compounds can be produced by processes analogous to the production process described above:

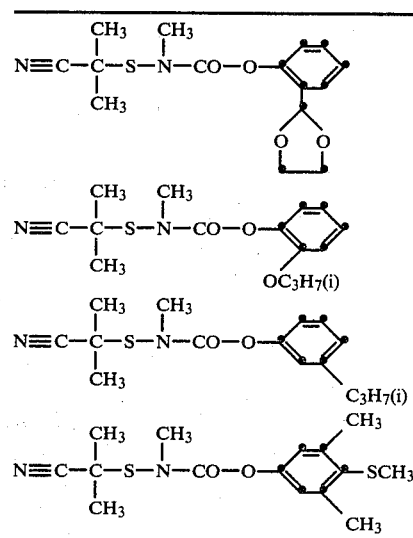

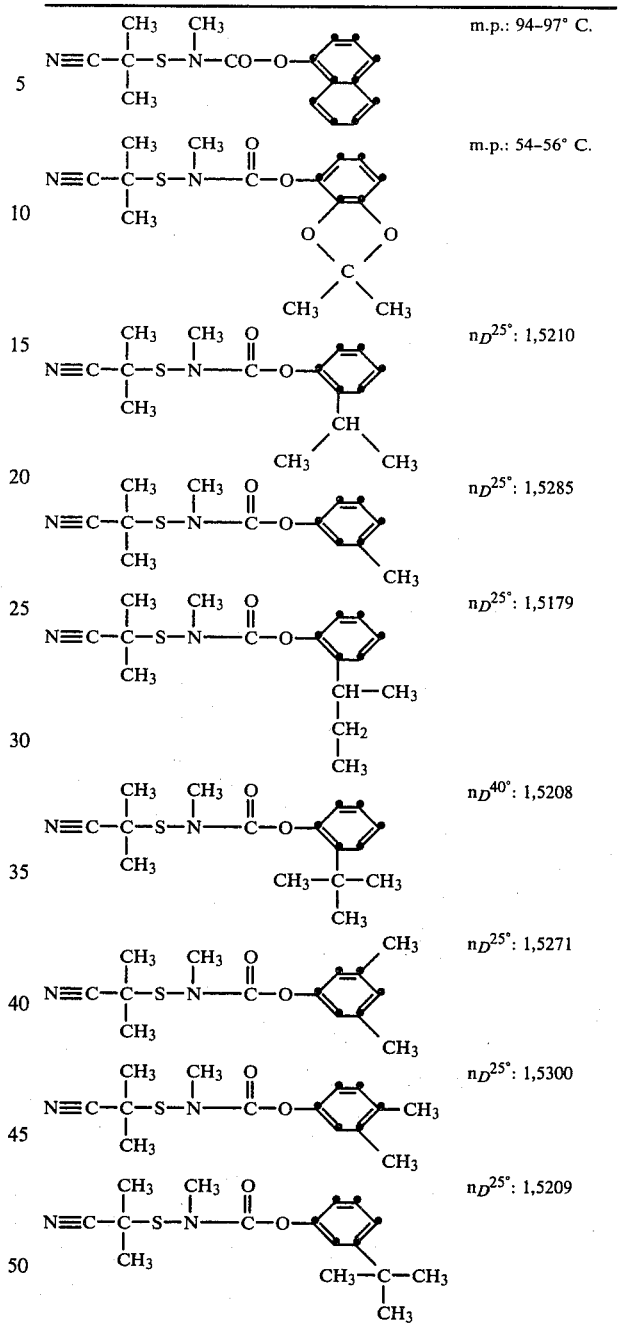

EXAMPLE 2

Insecticidal stomach-poison action: *Spodoptera littoralis*, *Dysdercus fasciatus* and *Heliothis virescens*

Cotton plants were sprayed with a test solution containing 50, 100, 200 and 400 ppm, respectively, of the compound to be tested. After the drying of the coating, larvae of the species *Spodoptera littoralis* (L3 stage), *Dysdercus fasciatus* (L4) and *Heliothis virescens* (L3), respectively, were settled onto the plants. Two plants were used per test compound and per test species, and an evaluation of the attained mortality rate was made after 2, 4, 24 and 48 hours. The test was carried out at 24° C. with 60% relative humidity.

Within the concentration limits given above, the compounds according to the Production Example 1 were 100% effective against larvae of the species *Spodoptera littoralis, Dysdercus fasciatus* and *Heliothis virescens.*

EXAMPLE 3

Insecticidal contact action: *Myzus persicae*

Plants (*Vicia fabae*) grown in water were each infested before commencement of the test with about 200 individuals of the *Myzus persicae* species. The plants treated in this manner were sprayed dripping wet 3 days later with a solution containing 10 and 1 ppm, respectively, of the compound to be tested, from a distance of 30 cm. Two plants were used per test compound and per concentration, and an assessment of the mortality rate attained was made after a further 24 hours.

Within the concentration limits given above, compounds according to Example 1 were 100% effective against insects of the species *Myzus persicae.*

EXAMPLE 4

Insecticidal systemic action: *Aphis craccivora*

Rooted bean plants were transplanted to pots each containing 600 ccm of soil; and 50 ml of a test solution containing 25 ppm, 5 ppm and 1 ppm, respectively, of the compound to be tested was subsequently poured directly onto the soil. After 24 hours, aphids (*Aphis craccivora*) were settled onto the parts of plants above the soil, and a plastics cylinder was placed over the plants and drawn to by tying at the bottom in order to protect the aphids from any contact or gas action of the test substance. The evaluation of the mortality rate achieved was made 24 and 48 hours after commencement of the test. Two plants, each in a separate pot, were used per concentration level of test substance. The test was carried out at 25° C. with 70% relative humidity.

Within the concentration limits given above, compounds according to Example 1 had a 100% systemic action against insects of the species *Aphis craccivora.*

What is claimed is:

1. An N-(2-isobutyronitrilesulfenyl)-N-methyl carbamate of the formula

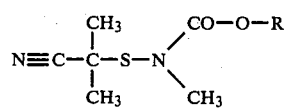

wherein R is 2,2-dimethyl-(2H,3H)-dihydrobenzofuran-7-yl, α-naphthyl,

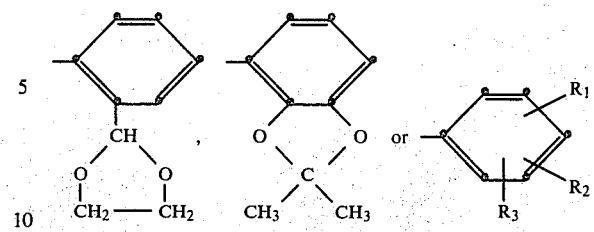

and $R_1$, $R_2$ and $R_3$ are each hydrogen, $C_1$-$C_5$-alkyl, $C_1$-$C_5$-alkoxy or $C_1$-$C_5$-alkylthio.

2. A compound according to claim 1, wherein R is 2,2-dimethyl-(2H,3H)-dihydrobenzofuran-7-yl, α-naphthyl,

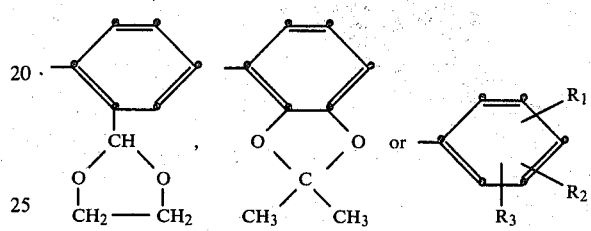

$R_1$ is hydrogen or $C_1$-$C_5$-alkyl, and $R_2$ and $R_3$ are each hydrogen, methyl, isopropoxy or methylthio.

3. The compound according to claim 2 of the formula

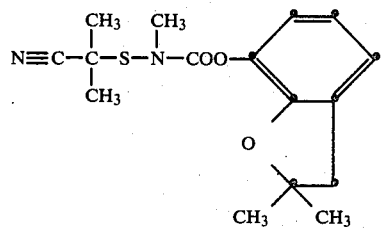

4. The compound according to claim 2 of the formula

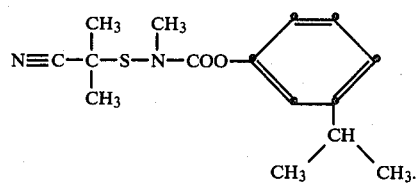

5. A pesticidal composition containing as active ingredient 0.1 to 99% of a compound according to claim 1, and at least 0 to 25% of a tenside as well as 1 to 99.9% of a solid or liquid additive.

6. A method for combating insects and acarids on animals and plants which comprises applying thereto an insecticidally or acaricidally effective amount of a compound accordingly to claims 1, 2, 3 or 4.

* * * * *